US00PP29758P3

(12) United States Plant Patent
Ammerlaan

(10) Patent No.: US PP29,758 P3
(45) Date of Patent: Oct. 16, 2018

(54) *ECHEVERIA* PLANT NAMED 'OVGRPP'

(50) Latin Name: ***Echeveria* hybrid**
Varietal Denomination: OVGRPP

(71) Applicant: Johannes Hendrikus Adrianus Ammerlaan, Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/731,659

(22) Filed: Jul. 13, 2017

(65) Prior Publication Data

US 2018/0092281 P1 Mar. 29, 2018

(30) Foreign Application Priority Data

Sep. 29, 2016 (QZ) ..... PBR 2016/2371

(51) Int. Cl.
*A01H 5/02* (2018.01)
*A01H 5/12* (2018.01)

(52) U.S. Cl.
USPC ..... Plt./373
CPC ..... *A01H 5/12* (2013.01)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Echeveria* cultivar named 'OVGRPP' which is characterized by a flattened globular plant form with greyed-purple foliage, narrowly margined pink and becoming red-purple with maturity, arranged in a basal rosette borne on a short stem. The foliage is moderately pruinose which creates a distinct bluish hue. The new variety has shown to be uniform and stable in the resulting generations from asexual propagation.

4 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'OVGRPP'.

CROSS REFERENCE TO RELATED APPLICATIONS

This application claims priority to the Community Plant Variety Rights application number 2016/2371, filed Sep. 29, 2016, which is herein incorporated by reference.

BACKGROUND OF THE INVENTION

Parentage: 'OVGRPP' is a spontaneous, naturally occurring whole-plant mutation of *Echeveria* 'Perle Von Nürnberg' (not patented) which was discovered by the inventor in April of 2009 at a commercial greenhouse in Bleiswijk, The Netherlands. The mutation was noted for its thick, robust pink to red foliage by comparison to the thinner, weaker greyed-purple foliage of the parent plant.

Asexual Reproduction: Asexual reproduction of the new cultivar 'OVGRPP', by way of rooting leaf cuttings, was first initiated in September of 2009 at the inventor's commercial greenhouse in Bleiswijk, The Netherlands. Through ten subsequent generations, the unique features of this cultivar have proven to be stable and true to type.

SUMMARY OF THE INVENTION

The cultivar 'OVGRPP' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVGRPP'. These characteristics in combination distinguish 'OVGRPP' as a new and distinct *Echeveria* cultivar:

1. 'OVGRPP' exhibits a flattened globular plant form with foliage arranged in a basal rosette which eventually forms a short, unbranched stem with age; and
2. 'OVGRPP' exhibits broad spatulate foliage and an apiculate apex with a slight upwardly curved attitude; and
3. 'OVGRPP' exhibits moderately pruinose foliage, which gives the foliage a bluish hue; and
4. 'OVGRPP' exhibits juvenile foliage with a greyed-purple general coloration, suffused with red towards the base, and pink margins, the colors becoming more intense with exposure to ultraviolet light; and
5. 'OVGRPP' exhibits mature foliage with a greyed-purple general coloration and red-purple margins, the colors becoming more intense with exposure to cooler temperatures.

BOTANICAL DESCRIPTION OF THE PLANT

Figure 1:
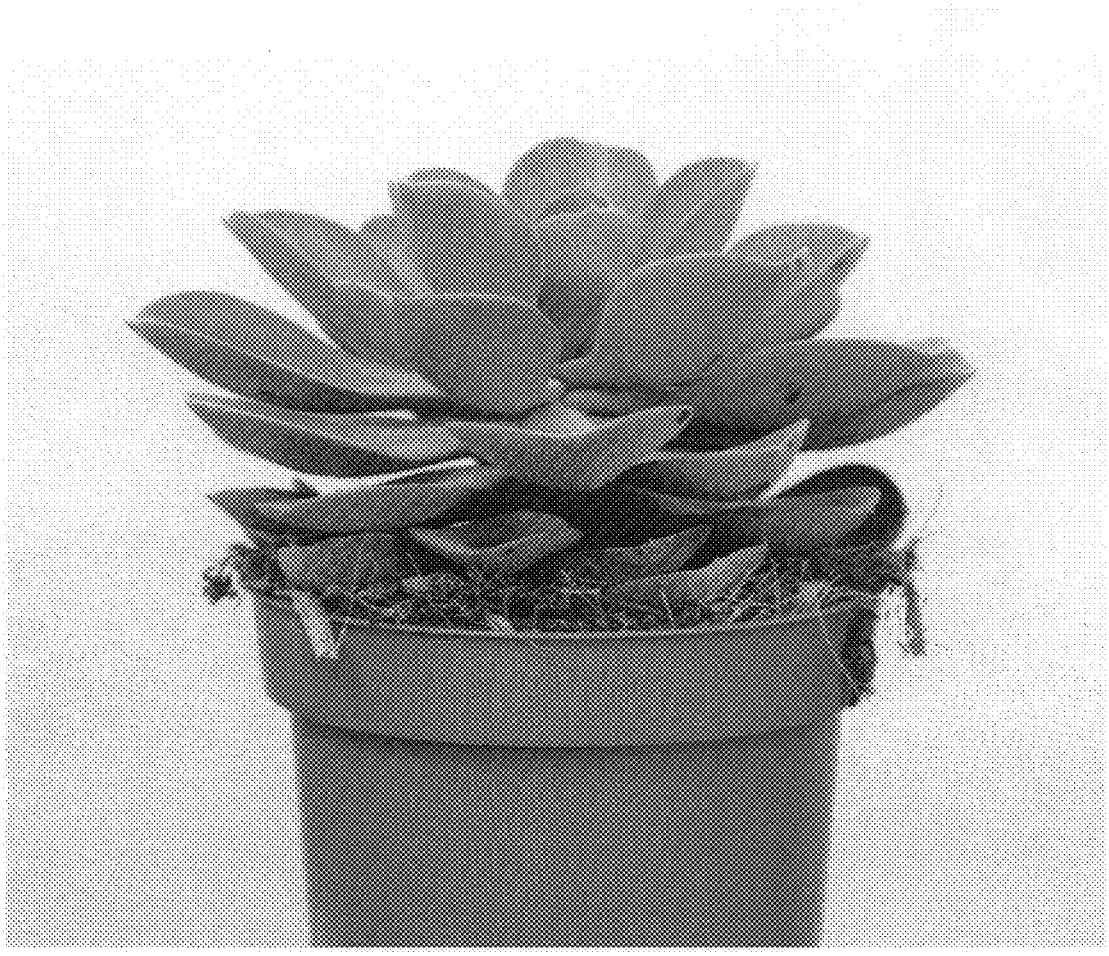
FIG. 1 illustrates, as nearly true as it is reasonably possible to make the same in color photographs of this type, an exemplary plant of 'OVGRPP' grown in a commercial greenhouse in Bleiswijk, The Netherlands. This plant is approximately 5 months old, shown planted in an 11 cm container.
Figure 2:
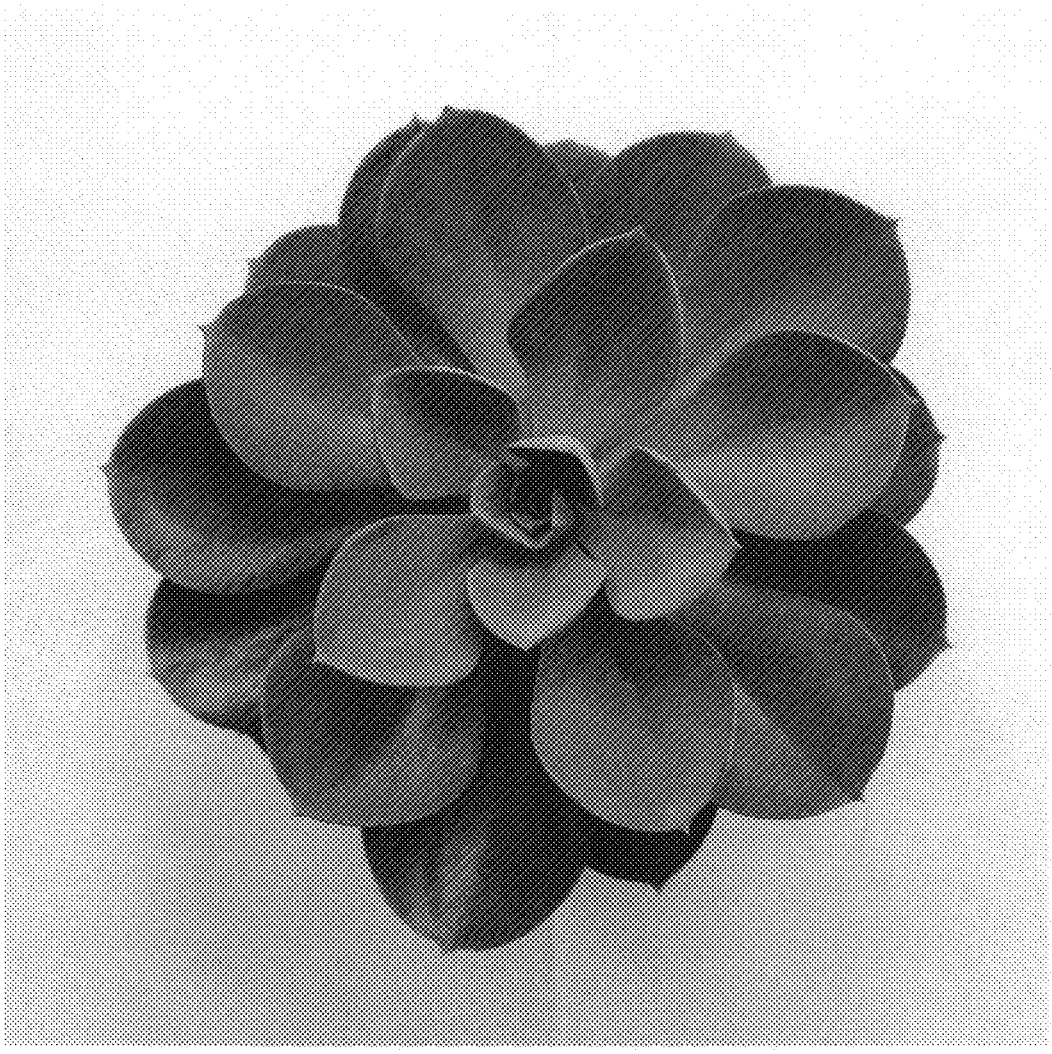
FIG. 2 illustrates, as nearly true as it is reasonably possible to make the same in color photographs of this type, the typical foliage arrangement of 'OVGRPP'.
Figure 3:
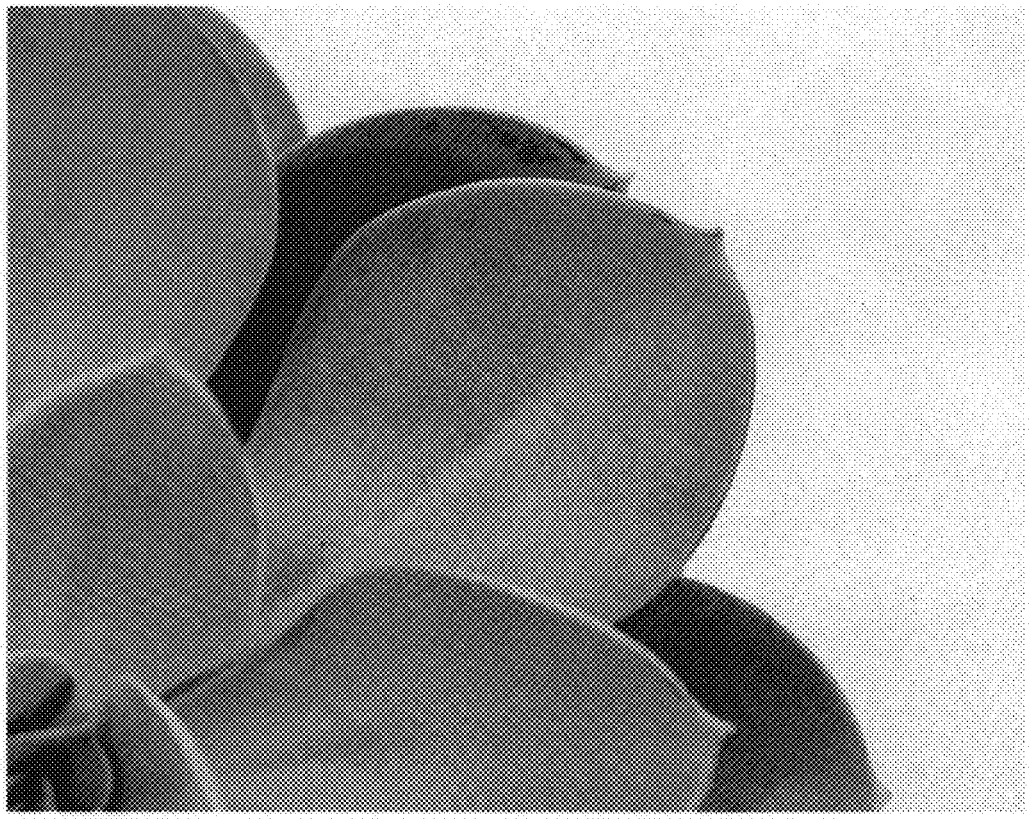
FIG. 3 illustrates, as nearly true as it is reasonably possible to make the same in color photographs of this type, the adaxial surface of the mature foliage 'OVGRPP'.
Figure 4:
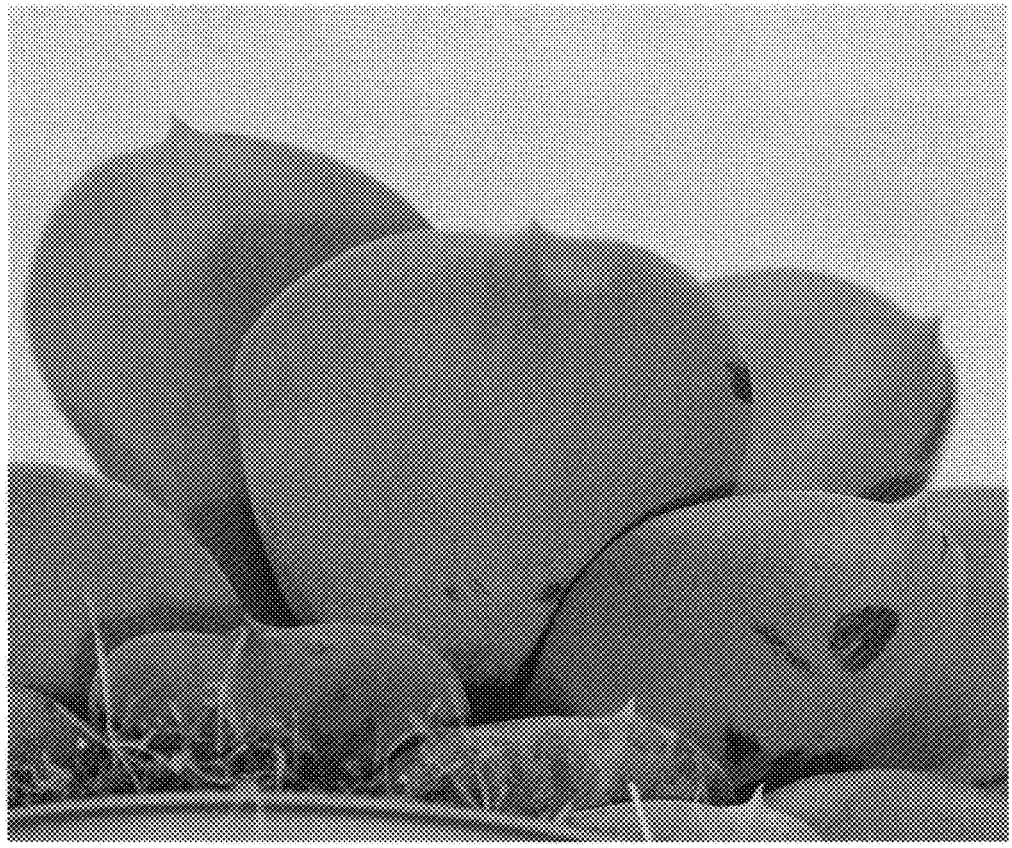
FIG. 4 illustrates, as nearly true as it is reasonably possible to make the same in color photographs of this type, the abaxial surface of the mature foliage 'OVGRPP'.

The following observations and measurements made in November of 2016 describe averages from a sample set of six specimens of 5 months old 'OVGRPP' plants grown in 11 cm nursery containers at commercial greenhouse in Bleiswijk, The Netherlands. Plants were produced using conventional greenhouse production protocols for *Echeveria* which consisted of minimal irrigation, by way of ebb and flow benches, and fertilizer applications. No chemical pest and disease control were utilized. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVGRPP' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVGRPP' and a comparison with the parent and closest known comparator, *Echeveria* 'Perle Von Nürnberg', is provided below.

Plant description:

*Growth habit*.—Succulent perennial with foliage growing in a non-branched basal rosette.

*Plant shape*.—Flattened globular.

*Height from soil level to top of foliar plane*.—9.4 cm.

*Plant spread*.—Average of 15.3 cm.

*Growth rate*.—Low.

*Plant vigor*.—Low.

*Propagation*.—Type — Leaf cuttings. Time to initiate rooting — Approximately 30 days at an approximate temperature of 20 degrees Celsius. Crop time — Approximately 5 months to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosettes, eventually forming a short, unbranched stem with age; no lateral branching.

*Quantity of main stems*.—1.

*Main stem dimensions*.—6.0 cm long and 1.0 cm in diameter.

*Internode length*.—0.25 cm.

*Cross section*.—Rounded.

*Aspect*.—Nearly vertical.

*Strength*.—Moderately strong.

*Texture and luster*.—Glabrous and matte, due to a waxy layer covering the stem.

*Color, when developing*.—Yellow-green, nearest to RHS 145C, and suffused with greyed-purple, nearest to RHS 185D but lighter; stem covered with a waxy layer colored purple, in between RHS 76C and 76D.

*Color of mature stem*.—Yellow-green, nearest to RHS 145C, and heavily suffused with greyed-purple, nearest to RHS 185D but lighter; stem covered with a waxy layer colored purple, in between RHS 76C and 76D.

*Color at internodes*.—Yellow-green, nearest to RHS 145C, and heavily suffused with greyed-purple, nearest to RHS 185D but lighter; stem covered with a waxy layer colored purple, in between RHS 76C and 76D.

Foliage:

*Arrangement*.—Rosette.

*Division*.—Simple.

*Attachment*.—Sessile.

*Quantity*.—Approximately 24 leaves per rosette.

*Shape*.—Thick, succulent leaves which are spatulate.

*Dimensions*.—7.0 cm long, 3.7 cm wide, and 0.4 cm thick, on average.

*Aspect*.—Moderately concave; slightly curved upwards.

*Attitude*.—Very slightly curved upward.

*Apex*.—Short apiculate.

*Base*.—Cuneate.

*Margin*.—Entire; not undulated or lobed.

*Pubescence, texture and luster of the adaxial surface*.—Glabrous, smooth, and slightly glossy; moderately pruinose, colored nearest to a mixture of greyed-purple to black, RHS N187B and 202B, but appearing as more of a bluish coloration (no correlating to an RHS color designation).

*Pubescence, texture and luster of the abaxial surface*.—Glabrous, smooth, and slightly glossy; moderately pruinose, colored nearest to a mixture of greyed-purple to black, RHS N187B and 202B, but appearing as more of a bluish coloration (no correlating to an RHS color designation); bluish coloration of the abaxial surface is lighter than that of the adaxial surface.

*Color*.—Juvenile foliage, adaxial surface — Greyed-purple, in between RHS N186C and 187A, and suffused with red towards the base, nearest to RHS 53C; narrowly margined pink, nearest to RHS 68C. Juvenile foliage, abaxial surface — Greyed-purple, in between RHS N186C and 187A, and suffused with red towards the base, in between RHS 53B and 53C; narrowly margined pink, nearest to RHS 68C. Mature foliage, adaxial surface — Nearest to in between greyed-purple, RHS N186C, and brown, RHS 200A; fading to greyed-purple towards the base, nearest to RHS 185A; narrowly margined red-purple, RHS 67B. Mature foliage, abaxial surface — Brown, in between RHS 200B and 200C, and fading to in between red and greyed-purple towards the base, RHS 53B and 185A; narrowly margined red-purple, RHS 67B.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT

Plants of the new cultivar 'OVGRPP' differ from the parent, *Echeveria* 'Perle Von Nürnberg' in the following characteristics described in Table 1 below.

TABLE 1

| Characteristic | 'OVGRPP' | 'Perle Von Nürnberg' |
|---|---|---|
| Plant shape. | More open and upright. | More compact. |
| General coloration of the mature foliage. | More greyed-purple; more pruinose. | Less greyed-purple; less pruinose. |
| Leaf margin coloration of the mature foliage. | Red-purple. | Pink. |

COMPARISONS WITH THE CLOSEST KNOWN COMPARATOR

Plants of the new cultivar 'OVGRPP' differ from the closest known comparator, *Echeveria* 'Purple Pearl' (Community Plant Variety Rights Office grant number 2008/2720), which is also the closest known comparator, in the following characteristics described in Table 2 below.

TABLE 2

| Characteristic | 'OVGRPP' | 'Purple Pearl' |
|---|---|---|
| General coloration of the mature foliage. | Greyed-purple. | Purple. |
| Abundance of pruinose on the foliage, | More pruinose, creating a deep bluish coloration, | Less pruinose; bluish coloration is not as pronounced. |
| General coloration of the aging foliage, | Older leaves are less suffused with green; retaining the bluish coloration. | Older leaves are more suffused with green. |

That which is claimed is:

1. A new and distinct variety of *Echeveria* plant named 'OVGRPP', substantially as described and illustrated herein.

* * * * *